(12) United States Patent
Nenu et al.

(10) Patent No.: US 9,199,894 B2
(45) Date of Patent: Dec. 1, 2015

(54) ISOMERISATION CATALYST PREPARATION PROCESS

(75) Inventors: Nicoleta Cristina Nenu, Amsterdam (NL); Bart Pelgrim, Amsterdam (NL)

(73) Assignee: Shell Oil Company, Houston, TX (US)

( * ) Notice: Subject to any disclaimer, the term of this patent is extended or adjusted under 35 U.S.C. 154(b) by 260 days.

(21) Appl. No.: 13/885,951

(22) PCT Filed: Nov. 16, 2011

(86) PCT No.: PCT/EP2011/070193
§ 371 (c)(1),
(2), (4) Date: Jun. 13, 2013

(87) PCT Pub. No.: WO2012/066012
PCT Pub. Date: May 24, 2012

(65) Prior Publication Data
US 2014/0179969 A1   Jun. 26, 2014

(30) Foreign Application Priority Data

Nov. 18, 2010   (EP) ..................... 10191702

(51) Int. Cl.
*C07C 5/27* (2006.01)
*B01J 23/42* (2006.01)
*B01J 29/74* (2006.01)
*B01J 37/02* (2006.01)

(52) U.S. Cl.
CPC .............. *C07C 5/2791* (2013.01); *B01J 23/42* (2013.01); *B01J 29/7469* (2013.01); *B01J 37/0213* (2013.01); *C07C 5/2724* (2013.01); *C07C 2521/04* (2013.01); *C07C 2523/42* (2013.01); *C07C 2529/70* (2013.01)

(58) Field of Classification Search
USPC ................................. 585/481, 502
See application file for complete search history.

(56) References Cited

U.S. PATENT DOCUMENTS

| | | | |
|---|---|---|---|
| 3,832,449 A * | 8/1974 | Rosinski et al. ............ | 423/705 |
| 3,856,872 A | 12/1974 | Morrison | |
| 4,485,185 A | 11/1984 | Onodera et al. | |
| 4,762,957 A | 8/1988 | Sachtler et al. | |
| 4,899,012 A | 2/1990 | Sachtler et al. | |
| 4,939,110 A | 7/1990 | Sachtler et al. | |
| 5,053,558 A * | 10/1991 | Sachtler ................ | C07C 5/2791 |
| | | | 568/780 |
| 6,576,120 B1 * | 6/2003 | Van Ballegoy et al. ....... | 208/119 |
| 6,652,832 B2 | 11/2003 | Malek | |
| 6,709,570 B1 | 3/2004 | van Crijnen et al. | |
| 7,495,137 B2 | 2/2009 | Zhou et al. | |
| 2007/0004947 A1 | 1/2007 | Zhou et al. .................... | 585/481 |

FOREIGN PATENT DOCUMENTS

| | | | |
|---|---|---|---|
| CN | 10154149 | 2/1992 | |
| CN | 1376089 | 10/2002 | |
| CN | 1715370 | 1/2006 | |
| EP | 1547684 | 6/2005 | ............... B01J 29/70 |
| WO | 9745198 | 12/1997 | |
| WO | 2004046034 | 6/2004 | |
| WO | WO2010000652 | 1/2010 | ............... B01J 29/74 |

OTHER PUBLICATIONS

Jeffrey T. Miller, Marc Schreier, A. Jeremy Kropf, and John R. Regalbuto. "A fundamental study of platinum tetraammine impregnation of silica 2. The effect of method of preparation, loading, and calcination temperature on (reduced) particle size". Journal of Catalysis 225 (2004) 203-212.*
Spieker et al. "A fundamental model of platinum impregnation onto alumina", Chemical Engineering Science 56 (2001) 3491-3504.*
Pines et al. "Alumina: Catalyst and Support. I. Alumina, its Intrinsic Acidity and Catalytic Activity", J. Am. Chem. Soc. 1960, 82 (10), pp. 2471-2483.*
Smirniotis, P.G. et al., "Effect of the Si/Al Ratio and of the Zeolite Structure on the Performance of Dealuminated Zeolites for the Reforming of Hydrocarbon Mixtures", Ind. Eng. Chem. Res. (1996) vol. 35, pp. 3055-5066.
Zhang, W.et al., "Dealuminated Zeolite-Based Composite Catalysts for Reforming of an Industrial Naphthene-Rich Feedstock", Applied Catalysis A: General vol. 168 (1998) pp. 113-130.
PCT International Search Report, Application No. PCT/EP2011/070193 dated Feb. 6, 2012.
International Search Report, Application No. PCT/EP2011/070195 dated Feb. 6, 2012.

* cited by examiner

*Primary Examiner* — In Suk Bullock
*Assistant Examiner* — Ali Z Fadhel
(74) *Attorney, Agent, or Firm* — Charles W. Stewart

(57) ABSTRACT

A process for preparing an alkylaromatics isomerisation catalyst comprising at least 0.01% wt of platinum on a carrier comprising of from 1 to 9 wt % of ZSM-12 and inorganic binder, which process comprises treating the carrier with an impregnation solution comprising a cationic platinum compound and having a pH of more than 9, and subsequently drying and calcining the impregnated carrier at a temperature of from 200 to 420° C.; and a process for the isomerisation of alkylaromatics with the help of catalyst thus obtained.

7 Claims, No Drawings

ISOMERISATION CATALYST PREPARATION PROCESS

PRIORITY CLAIM

The present application claims priority from PCT/EP2011/070193, filed Nov. 16, 2011, which claims priority from European application 10191702.9, filed Nov. 18, 2010, which is incorporated herein by reference.

This invention relates to a zeolite-based catalyst for the isomerisation of alkylaromatics, more specifically ethylbenzene.

Following fractionation or distillation of crude petroleum oil, a straight-run naphtha fraction is obtained. This fraction generally boils the 70° C. to 190° C. range, more specifically 80° C. to 150° C. at atmospheric pressure.

This naphtha fraction may be catalytically converted to an aromatic reformate. On conversion to reformate, the aromatics content is considerably increased and the resulting hydrocarbon mixture becomes highly desirable as a source of valuable chemical intermediates and as a component for gasoline.

The aromatic hydrocarbons present in the reformate generally contain 8 carbon atoms and include but are not limited to ethylbenzene and xylenes. Other components may be present such as their hydrogenated homologues for example naphthenes.

In many instances, it is desirable to further increase the content of highly desirable compounds by further conversion of aromatics. Many catalysts have been made and proposed for these reactions. However, for some reactions such as ethylbenzene isomerisation or transalkylation processes, there is commonly a trade-off between providing the desired products and known side reactions. The side reactions tend to give less desirable products such as compounds having of from 1 to 5 carbon atoms, toluene, benzene and compounds having 9 or more carbon atoms.

Within the xylenes, para-xylene is often the most desirable compound. O-xylene is the most desirable compound in only slightly less instances. Meta-xylene tends to be the least desirable compound. Isomerisation or transalkylation processes have been developed to specifically increase the amount of para-xylene or sometimes o-xylene. However, these processes tend to produce undesired side-products as mentioned above.

WO-A-2010/000652 describes alkylaromatics isomerisation catalysts comprising platinum on a carrier comprising 1-9 wt % ZSM-12 zeolite. Although these catalyst show a good performance, there is a continuous desire for further improvement. An important aspect of the performance of a catalyst is its activity. If a process is required to operate at high feed throughput, a high activity is crucial.

US-A-2007/0004947 describes an alkylaromatics isomerisation process using a first catalyst which is substantially free of a platinum-group metal and a second catalyst which comprises platinum-group metal and 10 to 90 mass-% of at least one molecular sieve. The platinum preferably is concentrated on the binder component which can be achieved by compositing the metal component with the binder prior to co-extruding the sieve and binder. In the absence of further compounds, a chloroplatinic solution as applied in Comparative Example 1 of US-A-2007/0004947 will be acidic.

The present invention relates to alkylaromatics isomerisation catalysts having improved activity. This improvement is attained by the use of a specific basic impregnation solution and a relatively low calcination temperature. Basic impregnation solutions tend not to be used because basic solutions generally extract silicon from the zeolite thereby making the structure unstable. WO-A-2010/000652 does not mention the pH of the platinum containing impregnation solution used. The impregnation exemplified in WO-A-2010/000652 was carried out at a pH below 3. Further, the exemplified calcinations were carried at a temperature of 450° C. and of 550° C.

It has now surprisingly been found that the specific basic impregnation solution of the present invention gives isomerisation catalysts having improved activity. Without wishing to be bound to any theory, it is thought that the high activity is attained by the fact that the cationic platinum component deposits on an almost atomic level on the zeolite of the carrier.

An object of the present invention is to prepare more active catalyst for the isomerisation of alkylaromatics more specifically for the isomerisation of a feed of alkylaromatics comprising 8 carbon atoms to obtain a product having an increased xylenes content and/or an increased para-xylene content as desired. For this, ethylbenzene is to be converted into xylene and/or meta-xylene into para-xylene, as desired.

According to the present invention, there is provided a process for preparing an alkylaromatics isomerisation catalyst comprising at least 0.01% wt of platinum on a carrier comprising of from 1 to 9 wt % of ZSM-12 and inorganic binder, which process comprises treating the carrier with an impregnation solution comprising a cationic platinum compound and having a pH of more than 9, and subsequently drying and calcining the impregnated carrier at a temperature of from 200 to 420 ° C.

Weight amounts mentioned in this description are on total weight of catalyst unless mentioned otherwise.

The expression isomerisation is used to indicate rearrangement of the carbons atoms within a molecule without substantially changing the number of carbon atoms of a molecule. However, side-reactions tend also to take place.

It is unexpected that an impregnation solution having a pH of more than 9 can be used for impregnation of a zeolitic carrier without negative effects on the zeolitic integrity. It is even more surprising that such impregnation gives a catalyst having improved activity. Besides the increased activity, the catalyst prepared according to the present invention gives an unexpected reduction of undesired side-products when compared with catalysts impregnated at mildly basic conditions.

The catalyst prepared according to the present invention can be used with a wide range of alkylaromatic compounds such as alkylaromatics comprising 8 carbon atoms or more, more specifically of from 8 to 12 carbon atoms. Preferably, the hydrocarbon feed mainly consists of alkylaromatic compounds comprising of from 8 to 10, more specifically of from 8 to 9, carbon atoms. The isomerisation of these compounds is known to follow similar reaction paths and uses the same or similar catalyst formulations. More specifically, the feed consists of at least 50% wt, more specifically at least 60% wt, most specifically at least 70% wt of alkylaromatic compounds comprising of from 8 to 10, more specifically of from 8 to 9, carbon atoms. Therefore, the present invention relates to the preparation of a catalyst for isomerisation of alkylaromatics in general, more specifically alkylaromatics comprising of from 8 to 10 carbons, more specifically alkylaromatics comprising 8 or 9 carbon atoms.

The impregnation solution for use in the present invention comprises a compound comprising cationic platinum which solution has a pH of more than 9, more specifically at least 10, more specifically at least 10.5, preferably at least 11, and most preferably at least 11.5.

Such high pH can be attained by adding base to the impregnation solution. The base can be any base known to be suitable to someone skilled in the art. Residue of the base which remains on or in the catalyst after calcining should not negatively interfere with the catalytic properties of the final catalyst. For this reason, it is generally preferred to use a basic compound according to the formula $(R_1R_2R_3NH)OH$ in which the compounds $R_1$, $R_2$, $R_3$ each independently are chosen from the group consisting of hydrogen and alkyl, more specifically chosen from the group consisting of hydrogen and an alkyl containing of from 1 to 6 carbon atoms, most specifically of from 1 to 4 carbon atoms. This class of compounds tends to be removed in full during calcination. Most preferably, the base is ammonium hydroxide.

The expression cationic platinum compound is used to indicate that platinum is present in the compound as a positively charged ion.

Compounds comprising cationic platinum, more specifically cationic platinum further surrounded by ligand such as ammonia, have the advantage that they tend to remain dissolved at basic conditions. Platinum compounds which are especially advantageous are platinum hydroxide compounds, more specifically those according to the formula $Pt(X)_n(OH)_2$ in which X is a ligand and n can be any integer of from 1 to 8, more specifically of from 1 to 5. X preferably is ammonia. The compound most preferably is tetrammine platinum hydroxide.

It will be appreciated that the impregnation solution generally will contain the compound in the dissolved form and not as the compound as such. The compounds generally are added to water to obtain the desired impregnation solution. However, it also is possible to form the compound in the impregnation solution by adding the required constituents as part of other compounds or compounds.

Base can be added to the impregnation solution together with the compound, beforehand or later. The specific compounds and bases applied influence which set-up is preferred. In many instances, it is preferred to combine metal compound and water and subsequently add the appropriate amount of base.

Impregnation can be carried out in any way known to someone skilled in the art. Preferred methods are pore volume impregnation and so-called continuously stirred impregnation. The latter involves contacting the carrier with an excess of impregnation solution while stirring. The impregnated carrier is subsequently removed from the impregnation solution.

The impregnated carrier is calcined at relatively low temperature in the preparation process according to the present invention namely of from 200° C. to 420° C. more preferably of from 250° C. to 400° C. It was found that calcination at a higher temperature reduced the activity of the catalyst.

The inorganic binder preferably is acidic and may be selected from any of the suitable acidic refractory metal oxides known in the art. The binder can be non-acidic when added but be converted into an acidic binder during calcination. For example, pseudo-boehmite converts into acidic gamma-alumina during calcination. Examples of preferred acidic inorganic binders is alumina optionally in combination with other compounds such as silica, alumina, titania, zirconia, ceria and/or gallia. Preferably, the binder consists of alumina with up to 50% wt of other compounds, more specifically up to 20% wt, more specifically up to 10% wt, most specifically up to 5% wt. Preferably, the binder consists of acidic alumina.

Alumina can be prepared in various forms. The alumina grades available differ in parameters such as pore volume, average pore diameter, bulk density, and surface area. Although different alumina manufacturers can provide the same or similar alumina products under different nomenclature, different products classifications can have the same or similar or overlapping criteria and/or properties. For example, "high pore" and "wide pore" aluminas tend to have the same or similar properties.

The present invention extends to the use of alumina as the inorganic binder from any source, and examples of suitable alumina binders include grades of the Pural range from Sasol, such as the KR and SB grades, and other wide pore aluminas such as WPA and HMPA from Criterion.

In a preferred embodiment of the present invention, the pore volume of the inorganic binder as measured with the help of nitrogen is at least 0.6 cc/g, preferably at least 1.2 cc/g; and the pore volume of the inorganic binder is up to 2 cc/g, preferably up to 1.6 cc/g.

These ranges of pore volume of the inorganic binder include 'wide pore' alumina, which has a more open structure to allow greater interaction with the alkylaromatics.

In another embodiment of the present invention, the average pore diameter of the inorganic binder is greater than 80 Å, preferably greater than 90 Å.

In a further embodiment of the present invention, the bulk density of the inorganic binder is less than 0.3, preferably less than 0.25 g/cc.

In a yet further embodiment of the present invention, the inorganic binder is present in an amount of more than 50% wt, more specifically more than 70 wt %, preferably more than 80 wt %, especially at least 90 wt %, based on total amount of catalyst.

The catalyst includes at least 0.01 wt % of platinum. Besides platinum, one or more other metals such as nickel and palladium can be present. Preferably, only platinum is present. The amount of platinum preferably is at least 0.05% wt, more preferably in the range of from 0.1 to 0.6 wt % based on total weight of catalyst.

The zeolite ZSM-12 is a well known zeolite, generally having an aluminosilicate basis, optionally including one or more other elements. Many methods of making various forms of ZSM-12 are known in the art. A definition of ZSM-12 is given in the Database of Zeolite Structures published in 2007/2008 on behalf of the Structure Commission of the International Zeolite Assocation.

The catalyst could be provided by admixture of the inorganic binder and zeolite components, following by shaping, and then typically drying and calcining the pre-former product. Optionally, the addition of the platinum compound is carried out after drying and/or calcining of the catalyst carrier. Preferably, the catalyst carrier is prepared by extrusion. Therefore, the catalyst carrier preferably is an extrudate.

In the present invention, it is particularly preferred that the ZSM-12 zeolite has:
an average crystal size in the range of 30 to 70 nm; and/or
a surface area as measured with the help of nitrogen adsorption of more than 250 m²/g, preferably more than 280 m²/g.

The size of the zeolite crystallites is determined by using X-ray diffraction and the Scherrer equation.

Additionally, it is preferred that the crystallinity of ZSM-12 is greater than 94%, preferably greater than 97%.

The zeolite as described above is known to those skilled in the art and is not further described herein.

The proportion of the catalyst being the ZSM-12 zeolite is preferably in the range 1-7 wt %, preferably 1-5 wt %, especially 3-5wt %, based on total amount of catalyst. Whilst the catalyst of the present invention may include a minor or very small amount of zeolite other than ZSM-12, the catalyst preferably comprises only ZSM-12 as the zeolite.

Another parameter of the zeolite ZSM-12 is its silica to alumina molar ratio (SAR). In the ethylbenzene isomerisation process, two different reactions overlap: ethylbenzene isomerisation and xylene isomerisation. Both reactions need acid sites to occur, and the acidity of the zeolite conventionally has been considered as having to be moderate. For this reason, conventional commercial catalysts have low SAR, and conventionally, it has been desired to maintain a relatively low SAR.

It is a particular feature of the present invention that the SAR of the zeolite preferably is in the range of from 60 to 200, more preferably in the range 70 to 150. This is because of the recognition that the acidity of inorganic binder can also contribute to the acidity of the catalyst for the reaction. Similarly, it was expected that a higher loading of zeolite in the catalyst would increase the catalyst activity. However, this turned out not to be required. The catalyst of the present invention has a lower than expected zeolite proportion namely at most 9 wt %, more specifically at most 8% wt, more specifically at most 7% wt and in particular less than 6.5 wt % based on total amount of catalyst.

The alkylaromatics isomerisation catalyst preferably consists of acidic inorganic binder, ZSM-12 zeolite having a SAR of from 60 to 200 and at least 0.1% wt of platinum.

The catalyst of the present invention is particularly suitable for the hydroisomerisation of ethylbenzene to xylenes, and for the isomerisation of xylenes to equilibrium. Further particularly, the catalyst of the present invention is suitable for use to provide para-xylene from ethylbenzene and other isomers of xylene commonly provided in mixed-component streams.

According to a further aspect of the present invention, there is provided a process for the isomerisation of alkylaromatics to provide a reaction mixture, which process comprises contacting a hydrocarbon stream comprising alkylaromatics with a catalyst prepared according to the present invention.

The hydrocarbon stream may comprise any amount of ethylbenzene, such as more than 60 wt % based on total amount of feedstock. The hydrocarbon stream specifically contains at most 60 wt % of ethylbenzene, more specifically at most 50% wt. Preferably, the hydrocarbon stream comprises at least 1% wt of ethylbenzene, more preferably at least 2% wt, more preferably at least 3% wt, more specifically at least 5% wt, more specifically at least 8% wt, preferably at least 10% wt, most preferably at least 15 wt %.

The hydrocarbon feed preferably is contacted with the catalyst at a temperature in the range of from 300 to 450° C., preferably at least 350° C. and preferably at most 400° C. Preferably, the pressure during isomerisation is of from 2 to 20 bar, more specifically of from 3 to 15 bar. The molar ratio of hydrogen to hydrocarbon of the feed preferably is of from 1 to 15 mol/mol, more specifically of from 2 to 10 mol/mol.

Of the xylenes present in the hydrocarbon feed, at least 20% generally will be in the form of meta-xylene, more specifically at least 30%, more specifically at least 40%, preferably at least 50%, more preferably at least 60%, most preferably at least 70%.

Examples of the present invention will now be described by way of example only.

EXAMPLES

Example 1

A ZSM-12/alumina catalyst carrier was prepared from 5 wt % of ZSM-12 having a SAR of 95, and 95 wt % of Criterion WPA alumina.

The mixture was kneaded and then shaped by extrusion into 1.6 mm cylinders. The extrudates were dried at 120° C.

An impregnation solution was prepared by adding $Pt(NH_3)_4(OH)_2$ to water and subsequently add $NH_4OH$ in such amount that the molar ratio of $NH_4OH$ to $Pt(NH_3)_4(OH)_2$ was 1.25. The impregnation solution was clear and had a pH of 12.4.

Freshly dried extrudates were contacted with an excess of impregnation solution and the mixture was stirred at a rotational speed of 50 rounds per minutes for about 3 hours.

The impregnated extrudates were separated from the impregnation solution and excess solution was removed. The extrudates thus obtained were dried at 120° C. and subsequently rotary calcined in air by increasing the temperature at a rate of 50 ° C. per hour to a temperature of 300 ° C. at which temperature the extrudates were kept for 1 hour before cooling down to room temperature.

The final catalyst contained 0.3% wt of platinum based on total weight of catalyst.

Example 2 (Comparative)

Impregnated extrudates prepared as described in Example 1 were dried at 120° C. and subsequently rotary calcined in air by increasing the temperature at a rate of 50 ° C. per hour to a temperature of 300 ° C. at which temperature the extrudates were kept for 1 hour and subsequently heated further at a rate of 50° C. per hour to a temperature of 475° C. and held there for 1 hour before cooling down to room temperature.

The final catalyst contained 0.3%wt of platinum based on total weight of catalyst.

Example 3 (Comparative)

An impregnation solution was prepared comprising $Pt(NH_3)_4Cl_2$ with $NH_4OH$ added to the impregnation solution to obtain a ratio of 0.28 mol $NH_4OH$/mol $Pt(NH_3)_4Cl_2$. The solution obtained was clear and had a pH of 8.3.

Freshly dried extrudates prepared as described in Example 1 were contacted with an excess of impregnation solution and the mixture was continuously stirred.

The impregnated extrudates were separated from the impregnation solution and excess solution was removed. The extrudates thus obtained were dried at 120° C. and subsequently rotary calcined in air by increasing the temperature at a rate of 50 ° C. per hour to a temperature of 300 ° C. at which temperature the extrudates were kept for 1 hour before cooling down to room temperature.

The final catalyst contained 0.3% wt of platinum based on total weight of catalyst.

Example 4 (Comparative)

An impregnation solution was prepared comprising hexachloroplatinic acid ($H_2PtCl_6$) as the metal source with nitric acid added to obtain pH of 1.6.

Extrudates prepared as described in Example 1 were pore volume impregnated with this impregnation solution. The extrudates thus obtained were dried at 120° C. and subsequently calcined at 450 ° C. for 1 hour.

The final catalyst contained 0.3% wt of platinum based on total weight of catalyst.

Example 5

The catalysts prepared in the above Examples were tested in the isomerisation of an ethylbenzene and mixed xylene mixture (comprising 19 wt % ethylbenzene (EB), 15.5 wt % ortho-xylene (OX), 59 wt % meta-xylene (MX) and 6.5 wt % ethyl cyclohexane).

The catalytic test was performed in a micro-flow reactor unit encompassing a reactor tube with an internal diameter of 15 mm, into which the catalyst was loaded together with SiC as packing material. After loading the catalyst was dried at 400° C. for 1.5 hours and then reduced with $H_2$ at 400° C. for 1 hour at a pressure of 8 bar. The reactor was then heated to 425° C. and treated with a mixture of 20 wt % EB and 80 wt % meta-xylene for a period of 24 hours at a weight hourly space velocity (WHSV) of 5 g feed/g catalyst/h and a $H_2$/hydrocarbon ratio of 4 mol/mol to reach a stable operation regime. Following this, the catalyst was subjected to a temperature of 387° C. and treated with the same EB and mixed xylene mixture described above (19 wt % EB, 15.5 wt % OX, 59 wt % MX and 6.5 wt % ethyl cyclohexane) at a WHSV of 4.5 g feed/g catalyst/h and a $H_2$/hydrocarbon ratio of 4 mol/mol.

The catalysts prepared in Examples 1, 2, 3 and 4 were compared for their ethylbenzene conversion (EB conversion), i.e. the weight percent of ethylbenzene converted by the catalyst into a xylene, i.e. either ortho-, meta- or para-xylene. The results are shown in Table 1.

TABLE 1

| Catalyst | EB conversion (% wt) |
|---|---|
| 1 | 39.5 |
| 2 (Comparative) | 31 |
| 3 (Comparative) | 29 |
| 4 (Comparative) | 34 |

Example 6

The catalysts of Examples 1 and 3 were tested further in the experimental set-up as described in Example 5.

The following expressions hereinafter have the following meaning.

C8 ring loss is the wt % of the starting compounds containing 8 carbon atoms and having a cyclic structure which are converted into compounds which do not contain a cyclic structure.

PXate is a measure for the degree to which the xylene reaction mixture has reached equilibrium for para-xylene. It is defined as follows:

$$PXate = \frac{\% \, w \, PX \text{ in Xylenes in product} - \% \, w \, PX \text{ in Xylenes in feed}}{\% \, w \, PX \text{ in Xylenes at equilibrium} - \% \, w \, PX \text{ in Xylenes in feed}}$$

where PX stands for para-xylene.

Table 2 shows the C8 ring loss at different PXate values.

Table 3 shows the amount and kind of products made at a PXate of 95.00.

TABLE 2

| | C8 ring loss (in % wt) at specified PXate | | | |
|---|---|---|---|---|
| Catalyst of Example | PXate = 95.00 | PXate = 96.00 | PXate = 97.00 | PXate = 97.5 |
| 1 | 2.8 | 3.3 | 3.8 | 4.4 |
| 3 | 3.2 | 3.6 | 4.3 | 4.9 |

TABLE 3

| | Product obtained (% wt on total product) | | | |
|---|---|---|---|---|
| Catalyst of Example | Hydrocarbons containing 1 to 4 carbon atoms | Toluene | Benzene | Aromatic compounds containing 9 carbon atoms |
| 1 | 0.7 | 0.75 | 0.25 | 1.1 |
| 3 | 0.9 | 0.74 | 0.26 | 1.2 |

It is clear from the above Tables 2 and 3 that impregnation at strongly basic conditions instead of mild basic conditions provides for a catalyst giving less undesirable side-products. Furthermore, this reduction in undesirable side-products is observed over a range of process conditions as shown by the improvement being attained at a variety of PXate values.

That which is claimed is:

1. A process for preparing an alkylaromatics isomerisation catalyst, which comprises at least 0.01%wt of platinum on a carrier comprising of from 1 to 9 wt % of ZSM-12 and a wide pore alumina binder, wherein the process comprises:
   mixing the wide pore alumina binder, having an average pore diameter greater than 80 Å, a nitrogen pore volume of at least 0.6 cc/g, and a bulk density of less than 0.3 g/cc, in an amount of more than 50 wt %, based on the total weight of catalyst, and zeolite ZSM-12, having a silica-to-alumina ratio (SAR) in the range of from 60 to 200, an average crystal size in the range of from 40 nm to 70 nm, and a surface area measured by the nitrogen adsorption method of more than 250 m$^2$/g, in an amount in the range of from 1 to 9 wt %, based on the total weight of catalyst, to provide an admixture of the wide pore alumina and the zeolite ZSM-12;
   shaping the admixture followed by drying without calcining the shapes to provide the carrier;
   treating the carrier with an impregnation solution having a pH of more than 9 and comprising a cationic platinum compound and a basic compound of the formula $(R_1R_2R_3NH)OH$, wherein $R_1, R_2, R_3$ each independently are chosen from the group consisting of hydrogen and alkyl containing from 1 to 6 carbon atoms, to provide an impregnated carrier;
   drying the impregnated carrier; and
   conducting a low-temperature calcination upon the impregnated carrier at a temperature in the range of from 250 to 400° C.

2. A process as claimed in claim 1 in which the impregnation solution further comprises ammonium hydroxide.

3. A process as claimed in claim 1 in which the impregnation solution has a pH of at least 11.

4. A process as claimed in claim 1 in which the ZSM-12 zeolite has a silica to alumina molar ratio (SAR) in the range of from 70 to 150.

5. A process as claimed in claim 1 in which the catalyst comprises at least 70 wt % of the wide pore alumina binder.

6. A process as claimed in claim 1 in which the cationic platinum compound is a platinum hydroxide compound.

7. A process for the isomerisation of alkylaromatics which process comprises contacting a hydrocarbon feed comprising alkylaromatics with a catalyst obtained in a process as claimed in claim 1.

* * * * *